United States Patent [19]

Grosse et al.

[11] Patent Number: 4,740,474

[45] Date of Patent: Apr. 26, 1988

[54] METHOD FOR DETERMINING THE PRESENCE OF DIBORANE IN AIR

[75] Inventors: Hans-Jörg Grosse; Helga Nietzschmann, both of Leipzig; Hartmut Merten; Klaus Plewinski, both of Dresden, all of German Democratic Rep.

[73] Assignee: Akademie der Wissenschaften der DDR Drägerwerk AG, German Democratic Rep.

[21] Appl. No.: 907,740

[22] Filed: Sep. 15, 1986

[30] Foreign Application Priority Data

Sep. 16, 1985 [DE]  Fed. Rep. of Germany ....... 2806262

[51] Int. Cl.$^4$ ............................................. G01N 21/71
[52] U.S. Cl. ...................................... 436/153; 436/182
[58] Field of Search ........................... 436/73, 153, 182

[56] References Cited

U.S. PATENT DOCUMENTS 4,447,543  5/1984  Harada et al. ................... 436/182

*Primary Examiner*—David L. Lacey
*Attorney, Agent, or Firm*—McGlew & Tuttle

[57] ABSTRACT

Diborane is detected in air with high sensitivity (ppb range) and selectivity. The invention is thus suitable for the monitoring of work places and rooms, the emission of plants, etc. The detection is based on an aerosol ionization gas analysis. In addition to an amine, a reagent which does not react with amine is added to the air stream and reacts with the diborane to form a compound which forms aerosols with the amine. The aerosols obtained by this reaction constitute the main measuring effect. When using $SO_2$ in concentration $\geq 3.5$ ppm, disturbances due to the $SO_2$ content of the air are eliminated.

6 Claims, No Drawings

4,740,474

METHOD FOR DETERMINING THE PRESENCE OF DIBORANE IN AIR

FIELD AND BACKGROUND OF THE INVENTION

The invention relates in general to gas detecting devices and methods and in particular to a new and useful method for determining the presence of diborane in the air.

The invention relates particularly to a method for the highly sensitive detection of diborane in air (ppb range) and operating with high selectivity and speed. It is thus suitable for monitoring work places and rooms, e.g. in micro-electronics in gaseous phase metering processes, or respectively the emission of plants as well as checking the tightness of installations and the like.

Various methods are used for the detection of diborane. Thus there are devices based on the principle of colorimetry. These devices have a detection range of from 0 to 87 ppb, being therefore sensitive and also selective, but they have a long time of enrichment of the compound to be detected (about one hour). Hence they are not suitable for cases of damage. Besides the strips have a limited shelf life; the cost of handling and maintenance is high.

A much faster method is based on dispersive infrared spectrometry (e.g. the MIRAN equipment line of the firm Foxboro Analytical, USA.) One measurement takes only about 10 seconds but the detection limit is as low as 100 ppb, so that many fields of use are left out.

Also chemoluminescence is used for the detection of diborane (e.g. FR No. 2,506,459). The radiation occurring in the reaction of diborane with ozone is measured with a secondary electron multiplier. This method, too, is fast, but the sensitivity is low. The detection limit is 2 ppm.

Lastly it is possible also to employ aerosol ionization gas analysis for the detection of diborane. A radioactive source produces in an ionization chamber an ionization current, which changes in the presence of aerosols, this change of the ionization current being proportional to the aerosol concentration. In the case of diborane, the reaction with an amine is utilized, which leads to well detectable aerosols. While the method is sufficiently fast, the sensitivity is not sufficient. The detection limit is 150 ppb. Besides, the sulfur dioxide content of the air causes a disturbance.

SUMMARY OF THE INVENTION

The invention provides the rapid, selective, and highly sensitive detection of diborane in air. It is the purpose of the invention to change the aerosol ionization analysis for diborane so that the detection limit is improved by more than one order of magnitude and the disturbing influence of atmospheric $SO_2$, if any, is eliminated.

The method according to the invention comprises that in addition to the amine (concentration $\geq 50$ ppm) there is added to the air stream a reagent which does not form aerosols with the amine, or does so only to a negligibly small extent, but reacts with the diborane to form compounds which form with the amine well detectable aerosols. The aerosols obtained by this reaction constitute the main measuring effect (besides the measuring effect caused by the direct reaction of the diborane with the amine).

Especially favorable is the use of sulfur dioxide in concentrations $\geq 3.5$ ppm, because then the $SO_2$ contained in the air has no, or only a negligibly slight, effect on the measurement ($SO_2$ barely reacts with amine).

To eliminate cross sensitivities against high acid reacting components in the air (e.g. $NO_2$, HCl) one uses granulated zinc which, while letting the diborane pass, eliminates strongly acid reacting substances by chemical reaction. In feeding the reagent into the air stream to be analyzed, this must be sure to occur before the addition of the amine, so that first the reaction of diborane with the reagent can take place. There are various possibilities to achieve this: Thus, the reagent may be proportioned into the air stream before the ionization chamber, while the amine is added directly into the ionization chamber, or a partial stream to which the reagent is added is separated from the air stream and is then recombined with the main stream, while the amine is again fed into the ionization chamber. Another possibility is to separate two partial streams from the air stream and to proportion into them the reagent and the amine, respectively. The partial streams are recombined with the main stream successively.

Feeding of the reagent can be done by different but known methods. For the use of $SO_2$ the following variant is recommended: By decomposition of $Na_2S_2O_5$ solution $SO_2$ is obtained, which permeates into the air stream through a suitable foil (e.g. polyethylene) in defined concentration. The advantage of this is that no liquids are needed in the measuring process itself.

Accordingly it is an object of the invention to provide an improved method for determining the presence of diborane in the air which comprises measuring on the basis of the aerosol ionization gas analysis with an amine by adding to the amine a reagent which does not react with the amine but which reacts with the diborane and produces a compound forming aerosol with the amine which has been added to the air stream.

A further object of the invention is to provide a method for detecting the presence of diborane which is simple to carry out and inexpensive to execute.

The various features of novelty which characterize the invention are pointed out with particularity in the claims annexed to and forming a part of this disclosure. For a better understanding of the invention, its operating advantages and specific objects attained by its uses, reference is made to the descriptive matter in which a preferred embodiment of the invention is illustrated.

DESCRIPTION OF THE PREFERRED EMBODIMENTS

The present invention refers to a method for determining the presence of diborane in the air. In accordance with the method of the invention the aerosol ionization gas analysis with an amine is used as a basis for determining the presence of diborane and this is effected by adding to the amine a reagent which does not react with the amine but which reacts with diborane and produces a compound forming aerosol with the amine which has been added to the air stream. The concentration of the reagent is chosen so that a greater measuring effect than that measuring effect caused by the direct reaction with the diborane and amine results. Preferably a sulfur dioxide in a concentration of at least 3.5 ppm is added. The sulfur dioxide is obtained by the decomposition of an aqueous $Na_2S_2O_5$ which is proportioned into the air stream by permeation. Preferably all acid reacting compounds are removed from the air stream by means of granulated zinc before the addition of a reagent and amine.

The apparatus used for carrying out the method of the invention comprises an ionization chamber with a built-in radiation source, devices for gas flow production, regulation and indication, data pickup and processing, storage vessels for amine and $Na_2S_2O_5$ solution, gas lines and gas separators. The determination of diborane is carried out as follows: An air stream is pumped into the apparatus with a pump. Filters installed at the gas inlet of the apparatus (granulated zinc and aerosol filters, respectively) remove all strongly acid reacting compounds and naturally occurring aerosols from the air stream. Then the air stream is divided into a main stream, which is conducted directly to the ionization chamber, and a partial stream, into which $SO_2$ is given by permeation through a polyethylene foil. The partial stream with the added $SO_2$ is recombined with the main stream before the ionization chamber. The amine is given into the ionization chamber, so that the formation of the aerosols to be detected occurs directly in the chamber. The concentrations of the amine are 50 ppm (saturation of the aerosol yield), those of the $SO_2$ approximately 3.5 ppm.

With the described apparatus, less than 5 ppb diborane can be measured in a measuring range of from 0 to 500 ppb. The measuring time is short ($\leq 1$ minute), the cost of maintenance is low.

While a specific embodiment of the invention has been shown and described in detail to illustrate the application of the principles of the invention, it will be understood that the invention may be embodied otherwise without departing from such principles.

What is claimed is:

1. A method for determining the presence of diborane in an air sample, comprising contacting an air sample containing diborane with an amine and a reagent reactable with diborane but not reactable with the amine, and in an ionizing chamber ionizing the amine, reagent, and air sample to form an aerosol to produce an ionization current and measuring the current as an indication of the quantity of diborane present in the sample.

2. A method according to claim 1, wherein acid reacting compounds are removed from the air stream by means of granulated zinc before the addition of the reagent and the amine.

3. A method according to claim 1, wherein said amine forms a direct reaction with diborane.

4. A method according to claim 3, wherein said reagent comprises sulfur dioxide, said sulfur dioxide being added to the air stream at a concentration of at least 3.5 parts per million.

5. A method according to claim 4, wherein said sulfur dioxide is first obtained by decomposition of an aqueous $Na_2S_2O_5$ solution and including proportioning the solution into the air stream by permeation.

6. A method according to claim 1, wherein said reagent comprises sulfur dioxide.

* * * * *